United States Patent [19]

Howe et al.

[11] 4,247,322
[45] Jan. 27, 1981

[54] 3-(M-TRIFLUOROMETHYLPHENYL)-5-HALOMETHYL ISOXAZOLES AS SAFENING AGENTS

[75] Inventors: Robert K. Howe, Bridgeton; Len F. Lee, Maryland Heights, both of Mo.

[73] Assignee: Monsanto Company, St. Louis, Mo.

[21] Appl. No.: 80,748

[22] Filed: Oct. 1, 1979

[51] Int. Cl.³ .................. A01N 43/00; A01N 37/18
[52] U.S. Cl. ........................................ 71/88; 71/118
[58] Field of Search ................................. 71/88, 118

[56] References Cited

U.S. PATENT DOCUMENTS

| 3,131,509 | 5/1964 | Hoffmann | 71/77 |
|---|---|---|---|
| 3,663,200 | 5/1972 | Olin | 71/118 |
| 3,884,671 | 5/1975 | Albright et al. | 71/88 |
| 3,959,304 | 5/1976 | Teach | 71/88 |
| 4,071,349 | 1/1978 | Arneklev et al. | 71/88 |
| 4,109,002 | 8/1978 | Davenport et al. | 424/272 |
| 4,129,568 | 12/1978 | Howe | 71/88 |
| 4,140,515 | 2/1979 | Howe | 71/88 |

Primary Examiner—Glennon H. Hollrah
Attorney, Agent, or Firm—Patricia A. Coburn; Donald W. Peterson

[57] ABSTRACT

Compounds of the formula:

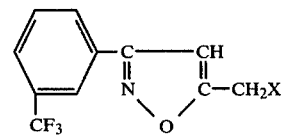

where X is chloro, bromo, fluoro or iodo, have been found to be effective in reducing herbicidal injury to direct seeded rice plants caused by 2-chloro-2',6'-diethyl-N-(butoxymethyl)acetanilide herbicide.

5 Claims, No Drawings

3-(M-TRIFLUOROMETHYLPHENYL)-5-HALOMETHYL ISOXAZOLES AS SAFENING AGENTS

This invention relates to 3-(m-trifluoromethylphenyl)-5-halomethyl isoxazoles which are useful in compositions and methods for reducing herbicidal injury. More specifically, the invention relates to novel compositions and methods for reducing injury to direct seeded rice plants by 2-chloro-2',6'-diethyl-N-(butoxymethyl) acetanilide (hereinafter referred to as butachlor) which comprises treating the rice plant locus or the seed of the rice plant with an effective amount of a 3-(m-trifluoromethylphenyl)-5-halomethyl-isoxazole compound, described more fully below.

BACKGROUND OF THE INVENTION

Butachlor is very useful for controlling weeds in the presence of growing crops, especially transplanted rice. Application of butachlor to direct seeded rice at rates necessary to kill or stunt weeds, however, injures the rice plant, slowing growth and development. Accordingly, butachlor is often undesirable for controlling weeds in the presence of direct seeded rice. Obviously, a safening agent consisting of a chemical compound that could be used to treat either the seed of the rice plant, the rice plant locus, or the rice plant itself, such that a reduction of injury due to application of the herbicide without a corresponding reduction of herbicidal action on the weed, would be quite beneficial.

DESCRIPTION OF THE INVENTION

In accordance with the novel aspects of the present invention, injury to rice due to application thereto of butachlor may be reduced without a corresponding reduction in injury to the weeds by application to the rice plant, the rice plant locus or the seed of the rice plant prior to planting, of an effective amount of a safening agent comprising a 3-(m-trifluoromethylphenyl)-5-halomethyl-isoxazole having the formula

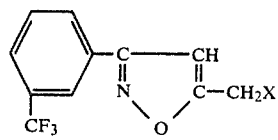

wherein X is chloro, bromo, fluoro or iodo. Preferably X is chloro or bromo and more preferably X is chloro.

Generally, the 3-(m-trifluoromethylphenyl)-5-halomethyl-isoxazoles of the foregoing formula may be prepared by the following method:

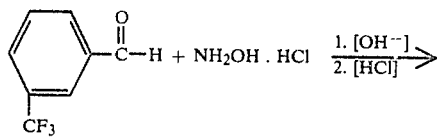

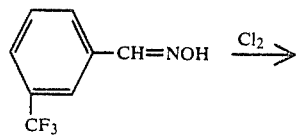

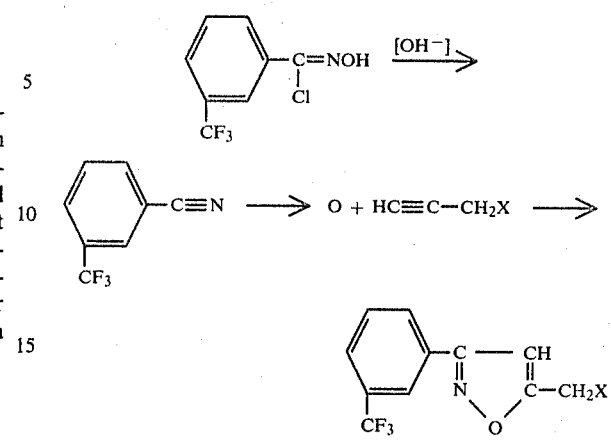

In order to more fully illustrate this procedure, the following examples are presented.

EXAMPLE 1

Preparation of 5-Bromomethyl-3-(m-Trifluoromethylphenyl)-Isoxazole

To a mixture of 200 g of m-trifluouromethylbenzaldehyde, 96.2 g of hydroxylamine hydrochloride, 460 ml of 50% EtoH water, 460 g of ice was added with vigorous stirring, 220 g of 50% sodium hydroxide solution. The mixture was stirred for one hour and extracted with ether. The aqueous layer was acidified with 114 ml of conc. HCl. The oil was separated and the aqueous layer was extracted with ether. The oil and ether were dried over drierite, concentrated under reduced pressure, to give 182 g of oil which solidified on standing. This material, m-trifluoromethylbenzaldehyde oxime, contained about 5% of EtoH (by nmr analysis) m.p. 39.5°–42.5° C. To a well stirred solution of 249 g (1.316 mole) of m-trifluoromethylbenzaldehyde oxime in 1.5 liters of chloroform in a 2 liter, four necked flask, was passed at 0°±2° C. with chlorine gas for 50 minutes, until the chlorine gas appeared on the gas bubbler. The chlorine gas was discontinued and the resulting green solution containing suspended white precipitate was stirred at 0° C. for one hour. Nitrogen was passed through the solution for two hours at 0° C. The reaction mixture was concentrated under reduced pressure to give 302 g of oil which when crystallized from petroleum ether (30°–75° C.) at low temperature, gave 198 g of white solid, m-trifluoromethylbenzhydroxamoyl-chloride, m.p. 49°–52.5° C., 67% yield. A solution of 44.6 g of m-trifluoromethylbenzhydroxamoylchloride in 500 ml of ether was thoroughly shaken with 200 g of cold 4% sodium hydroxide in a separatory funnel. The ether solution was separated, dried over CaSO$_4$ and placed in a three-necked 1 liter flask equipped with a mechanical stirrer. The ether solution was cooled to 10° C. and propargyl bromide (23.8 g, 0.2 mole) was added in one portion. The ether solution was allowed to warm to room temperature and thereafter was stirred for 18 hours. The ether solution was filtered to remove insoluble material, concentrated and the residue (50 g) was separated into two parts. 5 g of the residue was distilled at 1 mm (120°–130° C. pot temperature) on a Kugelrohr to give 4.2 g of an oil which was crystallized from hexane to give 2.5 g of white prisms m.p. 54.5°–56.0° C.

TLC of this material (silica gel, ether/hexane 1:1 as eluant) showed a single spot at $R_f=0.42$. 1.0 g of this solid was recrystallized at low temperature from toluene-hexane to give 0.7 g of white prisms m.p. 54.5°–56° C. The remaining 45 g of residue was crystallized from hexane to give 20 g of solid, m.p. 52°–55° C. The material showed a minor TLC spot at $R_f=0.66$, and a major spot at $R_f=0.42$. This solid was distilled on Kugelrohr to give 19.2 g of solid, m.p. 52°–54° C. The combined mother liquor was concentrated and distilled on a Kugelrohr at 4 mm (170° C. pot temperature) to give 19.2 g of solid-oil mixture which was crystallized from hexane at low temperature to give 13 g of yellow solid, m.p. 48°–55° C., which when recrystallized from toluene-hexane at low temperature gave 11.3 g of light yellow solid, m.p. 52°–54.5° C. The above solids were combined and recrystallized from toluene/hexane to give 26.7 g of solid, m.p. 52°–54° C.; additional 5.3 g of solid was isolated from the mother liquor, m.p. 51°–53° C., to give a combined yield of 54.7%.

Anal. Calc'd for $C_{11}H_7BrF_3NO$: C, 43.16; H, 2.31; N, 4.57; Br, 26.11. Found: C, 43.13; H, 2.32; N, 4.57; Br, 26.07.

EXAMPLE 2

Preparation of 5-Chloromethyl-3-(m-Trifluoromethylphenyl)-Isoxazole

To 17.6 g (0.0724 ml) of 3-(m-trifluoromethylphenyl)-5-isoxazole methanol (prepared as described in Example 1 except that propargyl alcohol was used instead of propargyl bromide) was added 50 ml of thionyl chloride dropwise under nitrogen. After complete addition of thionyl chloride, the reaction mixture was heated on a steam bath for 30 minutes, thereafter excess thionyl chloride was removed under reduced pressure. The residue was triturated with hexane and an oil precipitate resulted. After partial removal of hexane in a rotary evaporator under reduced pressure, the oil precipitate crystallized and was filtered to give a tan solid, mp 33°–36° C. The tan solid (6 g) was recrystallized from hexane to give 3.0 g of brown solid, mp 33°–37° C. which was Kugelrohr distilled (1 mm, 140° C.) to give 2.9 g of solid, mp, 36°–38° C. Combined filtrates were concentrated and the residue (14.8 g) was Kugelrohr distilled (1 mm, 140° C.) to give 13.6 g of yellow oil which crystallized upon standing, mp 29°–36.5° C.; total yield 16.5 g (87%).

Anal. Calc'd: C, 50.11; H, 2.70; N, 5.36. Found: C, 50.47; H, 2.70; N, 5.36

As noted previously, the 3-(m-trifluoromethylphenyl)-5-halomethyl isoxazole compounds may be used to protect rice plants from the herbicidal activity of butachlor herbicide without a corresponding diminution in herbicidal activity to the weeds. The amount of safening agent employed in the method and compositions of the invention will vary depending upon the manner of application, rate of application, environmental factors as well as other factors known in the art. In each instance, the amount employed is a safening effective amount, i.e., the amount which reduces crop injury by the herbicide. The amount of herbicide employed in the method and compositions of the invention is a "herbicidally effective amount", i.e., rates which produce effective controls of undesirable vegetation.

The safening agent may be applied to the plant locus in a mixture with the herbicide, sequentially, i.e., the antidote may be applied before or after the herbicide or it may be applied directly to the rice seed itself. By application to the "plant locus" is meant application to the plant growing medium, such as the soil, as well as the seeds, emerging seedlings, roots, stems, leaves, flowers, fruits or other plant parts.

To illustrate the effectiveness of the 3-(m-trifluoromethylphenyl)-5-halomethyl isoxazole compounds thereof, the following examples are presented. These examples are presented merely as being illustrative of the novel aspects of the invention and are not intended to be a limitation as to the scope thereof.

EXAMPLE 3

A good grade of top soil is placed in a container and compacted to a depth of approximately 1.27 cm. from the top of said container. A predetermined number of rice seeds are placed on top of the soil. A quantity of soil sufficient to substantially fill the container is measured and placed in a second container. A measured quantity of the safening agent dispersed or dissolved in a suitable carrier is applied to the soil in the second container. A measured quantity of butachlor herbicide dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and butachlor herbicide and the pots are leveled. The pots are then placed on a sand bench in the greenhouse and watered from below as needed. The plants are observed at the end of approximately 21 days and the results in terms of percent inhibition of each seed lot are recorded. For each test series, a pot is also prepared containing no butachlor herbicide and no safening agent as a control. Additionally, for each test, pots are prepared with soil covering the seed containing no butachlor herbicide and only the measured amount of safening agent being incorporated into the soil covering the seeds to ascertain any herbicidal effect of the safening agent alone. For each series of tests, the herbicidal effect of the butachlor herbicide is observed from pots treated with the same quantity of herbicide alone. The "safening effect" is determined by adding the herbicidal effect of the butachlor herbicide when applied alone to the herbicidal effect of the safening agent when applied alone (in no instance, however, will this sum be greater than 100) and subtracting from that the herbicidal effect obtained when both the herbicide and safening agent are incorporated into the soil as discussed above.

Table I summarizes the results obtained when the compounds of the invention were tested on rice plants in accordance with the procedure of Example 3 utilizing butachlor as the herbicide.

TABLE I

| Safening Agent Compound of Example No. | Rate of Safening Agent (kg/h) | Rate of Herbicide (kg/h) | Safening Effect |
|---|---|---|---|
| 1 | 8.96 | 6.72 | 48 |
| 2 | 8.96 | 6.72 | 60 |

EXAMPLE 4

A good grade of top soil is placed in a plastic pot. A measured quantity of the safening agent dispersed or dissolved in a suitable carrier is sprayed on the soil surface. A measured quantity of butachlor herbicide dissolved in a solvent is sprayed on the soil surface. Pre-soaked rice (in some instances a predetermined number of barnyardgrass weed seeds were also planted) is seeded into the pots that were previously flooded with water. The pots are flooded at least up to the soil surface for the duration of the test. The plants are observed at the end of approximately 21 days and the results in terms of the percent inhibition of rice are recorded. As in Example 3, for each test pots are prepared containing soil treated only with butachlor. For each test, pots are also prepared containing soil treated only with the safening agent. The safening effect is determined in accordance with Example 3.

Table II summarizes the results obtained when the compounds of the invention were tested on rice plants in accordance with the procedure of Example 4.

TABLE II

| Safening Agent Compound of Example | Rate of Safening Agent (kg/h) | Rate of Herbicide (kg/h) | Safening Effect | % Inhibition (Injury) Barnyard Grass |
|---|---|---|---|---|
| 1 | 0.56 | 0.07 | * | — |
|   | 0.56 | 0.28 | * | — |
|   | 0.56 | 1.12 | * | — |
| 2 | 0.56 | 0.07 | 60 | 100 |
|   | 0.56 | 0.28 | * | 100 |
|   | 0.56 | 1.12 | * | 100 |

*Safening effect was between 0 and 19

The above examples illustrate that the 3-(m-trifluoromethyl-phenyl)-5-halomethyl-isoxazoles of the present invention are useful in reducing butachlor herbicide injury to rice plants. The safening agent may be applied to the plant locus as a mixture, i.e., a mixture of a herbicidally effective amount of butachlor and a safening effective amount of safening agent, or sequentially, i.e., the plant locus may be treated with an effective amount of butachlor followed by a treatment with the safening agent or vice versa. The ratio of butachlor to safening agent may vary depending upon various factors, such as the weeds to be inhibited, mode of application, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixtures thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surfce-active agent and about 4 to 94 parts solvent, all parts being by weight based on the total weight of the composition.

The application of the herbicide, safening agent or mixtures thereof in a liquid or particulate solid form can be carried out by conventional techniques utilizing, for example, spreaders, power dusters, boom and hand sprayers, spray dusters and granular applicators. The compositions can also be applied from airplanes as a dust or spray. If desired, application of the compositions of the invention to plants can be accomplished by incorporating the compositions in the soil or other media.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of reducing injury to direct seeded rice injured by butachlor herbicide which comprises applying a non-phytotoxic, antidotally effective amount of a compound of the formula

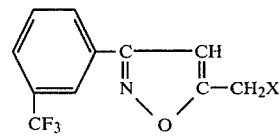

where X is chloro or bromo, to the soil surface or by pre-plant incorporation into the soil.

2. A method according to claim 1 wherein X is chloro.

3. A method according to claim 1 wherein X is bromo.

4. A method according to claim 1 wherein said antidotally effective compound is present at from about 1 to about 8 parts by weight for each part by weight of said butachlor herbicide.

5. A method according to claim 1 wherein said antidotal compound is applied to the soil.

* * * * *